United States Patent [19]

Kaplan et al.

[11] 4,335,244

[45] Jun. 15, 1982

[54] MONOLACTATE SALTS OF 4'-(9-ACRIDINYLAMINO)METHANESULFON-M-ANISIDIDE

[75] Inventors: Murray A. Kaplan, Syracuse; Alphonse P. Granatek, Baldwinsville, both of N.Y.

[73] Assignee: Bristol-Myers Company, New York, N.Y.

[21] Appl. No.: 150,401

[22] Filed: May 23, 1980

Related U.S. Application Data

[63] Continuation-in-part of Ser. No. 99,163, Nov. 30, 1979, abandoned.

[51] Int. Cl.$^3$ .................... C07D 219/10; A61K 31/47
[52] U.S. Cl. ...................................... 546/106; 424/257
[58] Field of Search .......................... 546/106; 424/257

[56] References Cited

U.S. PATENT DOCUMENTS 3,332,991 7/1967 Cannon .............................. 562/589
4,139,531 2/1979 Ledochowski et al. ............ 546/106
4,150,231 4/1979 Ledochowski et al. ............ 546/106

OTHER PUBLICATIONS

Legha et al., Cancer Research, 38, 3712–3716, (11/78).
Von Hoff et al., Cancer Treatment Reports, 62,(10), 1421–1426, (1978).
Issell, Cancer Treatment Reviews, 7, 73–83 (1980).
Lachman et al., The Theory and Practice of Industrial Pharmacy, 2nd ed., Lea & Febiger, Philadelphia, (1976), pp. 521–524.
Cain et al., Europ. J. Cancer, 10, pp. 539–549 (1974).
Kirk–Othmer, Encyclopedia of Chemical Technology, 2nd ed., vol. 12, (1967), p. 174.

*Primary Examiner*—Donald G. Daus
*Assistant Examiner*—Diana G. Rivers
*Attorney, Agent, or Firm*—David M. Morse

[57] ABSTRACT

This invention concerns three particular crystalline monolactate salts of the antitumor agent 4'-(9-acridinylamino)methanesulfon-m-anisidide. The salts are characterized in having unexpectedly high water-solubility.

7 Claims, 6 Drawing Figures

FIG. 1 INFRARED ABSORPTION SPECTRUM OF m-AMSA L(+)-MONOLACTATE HEMIACETONATE

NMR SPECTRUM OF m-AMSA L(+)-MONOLACTATE HEMIACETONATE

INFRARED SPECTRUM OF m-AMSA DL-MONOLACTATE ACETONE SOLVATE

NMR SPECTRUM OF m-AMSA DL-MONOLACTATE ACETONE SOLVATE

INFRARED ABSORPTION SPECTRUM OF m-AMSA D(-)-MONOLACTATE HEMIACETONATE

NMR SPECTRUM OF m-AMSA D(−)-MONOLACTATE HEMIACETONATE

4,335,244

MONOLACTATE SALTS OF 4'-(9-ACRIDINYLAMINO)METHANESULFON-M-ANISIDIDE

CROSS-REFERENCE TO RELATED APPLICATION

This application is a continuation-in-part application of our prior, co-pending application Ser. No. 99,163 filed Nov. 30, 1979 now abandoned.

BACKGROUND OF THE INVENTION

1. Field of the Invention

The novel acid addition salts of the present invention possess the advantageous antitumor properties of the known free base compound and in addition have unexpectedly high water-solubility, thus allowing preparation of useful clinical dosage forms for intravenous administration.

2. Description of the Prior Art

The acridine derivative m-AMSA [4'-(9-acridinylamino)methanesulfon-m-anisidide] was reported by Cain, et al. in *Europ. J. Cancer* 10:539–549 (1974) to possess significant antitumor activity in animal tumor systems. Since then, this compound has been subjected to clinical evaluation with very promising initial results.

When an antitumor agent such as m-AMSA is employed for human clinical use, it is recognized that solubility of the agent is often the controlling factor in determining route of administration and dosage forms. For instance, a water-soluble substance can be generally administered intravenously whereas a water-insoluble material is limited to other forms of parenteral administration such as intramuscular and subcutaneous. A therapeutic agent having water-solubility also facilitates preparation of oral and non-intravenous parenteral dosage forms for human administration. Thus, it is decidedly advantageous if a therapeutic agent is water-soluble, particularly when one considers that the most direct route for achieving therapeutic blood levels of a drug within the human body is by intravenous administration.

The free base form of m-AMSA has very limited solubility in water and thus cannot be used as a dosage form for intravenous administration. Attempts have been made to prepare acid addition salts to overcome this solubility problem, but the reported monohydrochloride and monomethanesulfonate salts also proved insufficiently water-soluble for clinical use. The formulation presently in clinical use consists of two sterile liquids combined prior to use. A solution of m-AMSA in anhydrous N,N-dimethylacetamide is contained in an ampule. A separate vial contains an aqueous L(+) lactic acid solution for use as a diluent. When mixed the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirable as a pharmaceutical vehicle.

It is accordingly an object of the present invention to provide a water-soluble, stable, therapeutically acceptable form of m-AMSA which can be administered intravenously (as well as by other routes) and which does not contain or require dimethylacetamide as a pharmaceutical vehicle. This object as well as other features and advantages of the invention will be readily apparent to those skilled in the art from the disclosure set out below.

SUMMARY OF THE INVENTION

The present invention provides novel water-soluble acid addition salts of m-AMSA which upon reconstitution with sterile water or a sterile aqueous vehicle can be administered intravenously and which do not have the disadvantages associated with the known intravenous forms of this agent. More particularly, there are provided (1) the crystalline L(+)-monolactate hemiacetonate of m-AMSA containing about 0.5 moles of acetone per mole of lactate salt, (2) the crystalline m-AMSA DL-monolactate acetone solvate containing from about 0.6 to 0.7 moles of acetone per mole of lactate salt and (3) the crystalline m-AMSA D(−)-monolactate hemiacetonate containing about 0.5 moles of acetone per mole of lactate salt.

DETAILED DESCRIPTION

Figure 1:
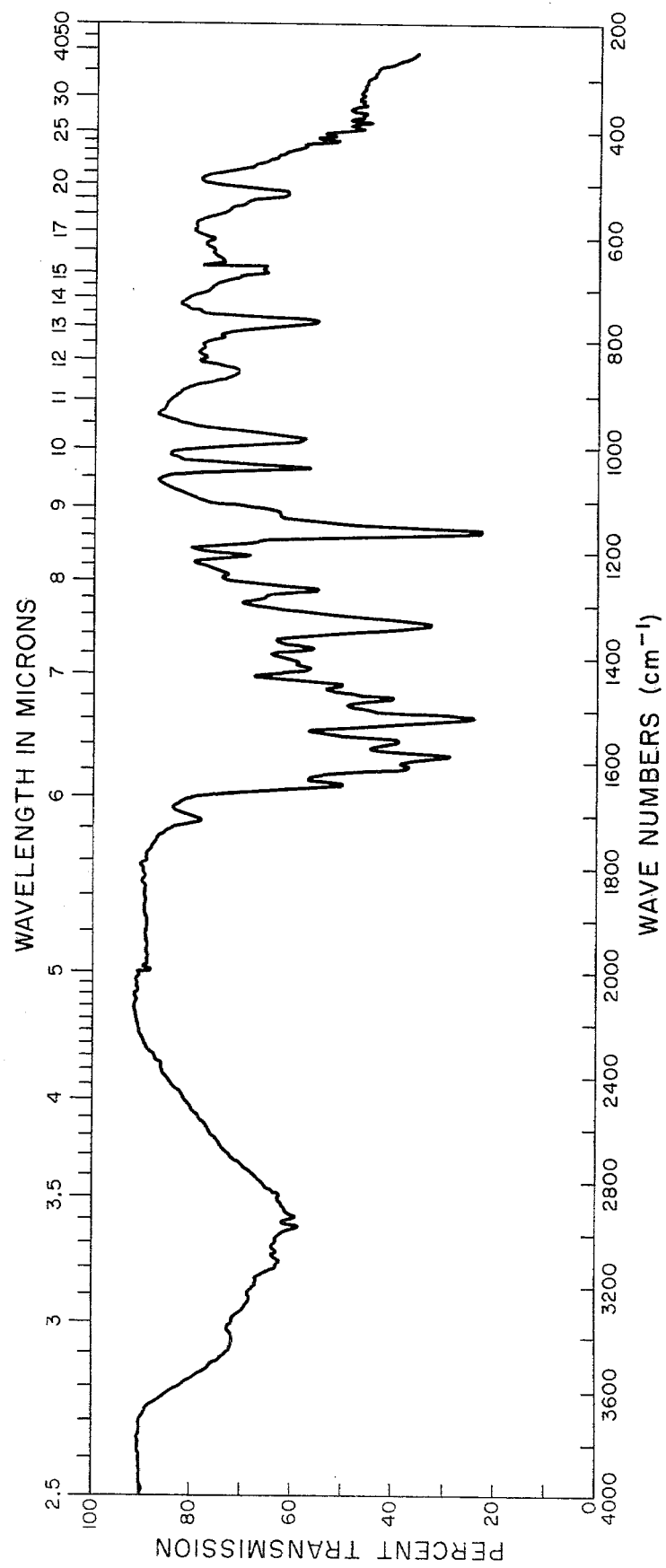
FIG. 1 shows the infrared absorption spectrum of m-AMSA mono L(+)-lactate hemiacetonate when pelleted in potassium bromide.
Figure 2:
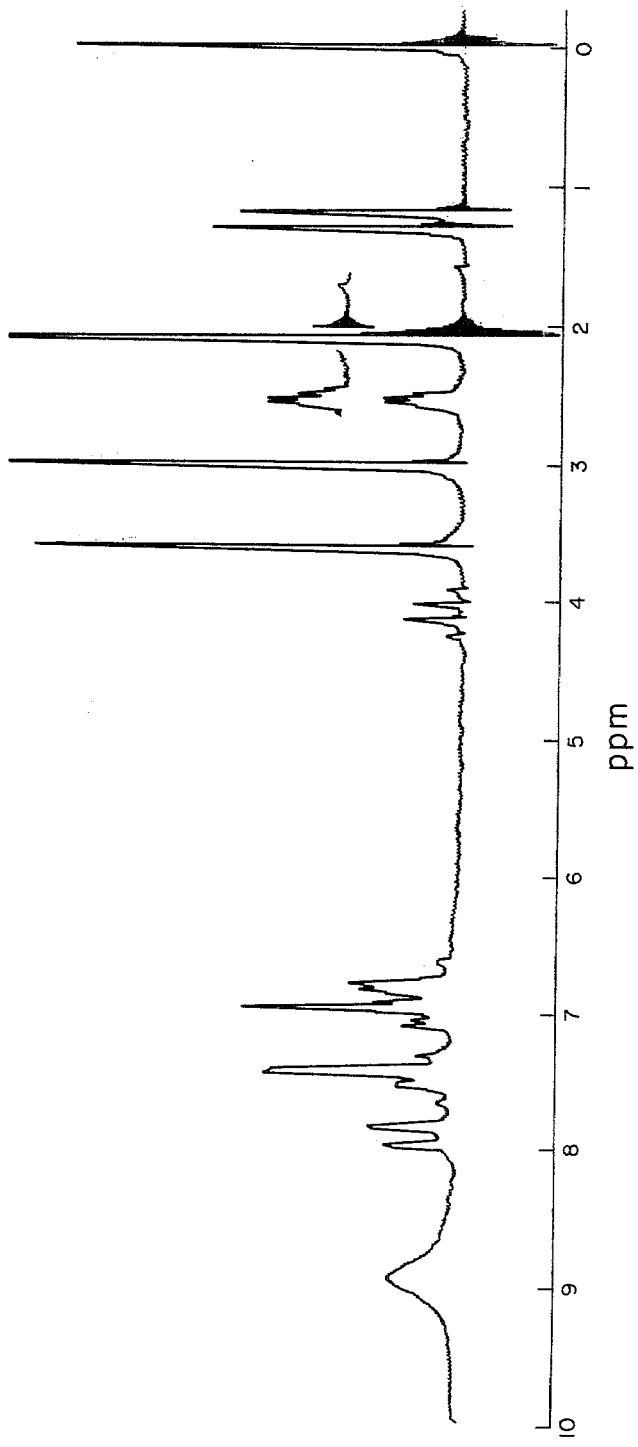
FIG. 2 shows the NMR spectrum of m-AMSA mono L(+)-lactate hemiacetonate in dimethylsulfoxide (100 MHz).

Many conventional pharmaceutically acceptable acid addition salts of m-AMSA are only slightly soluble in water and are thus unsuited for preparation of aqueous intravenous solutions. This is evident from literature references to the hydrochloride and methanesulfonate salts as well as from solubility tests carried out by the present inventors on salts such as the sulfate, levulinate and citrate.

In investigating solubility properties of m-AMSA acid addition salts, we have unexpectedly found that the crystalline acetone solvates of m-AMSA L(+)-monolactate, D(−)-monolactate and DL-monolactate possess sufficiently high water-solubility at room temperature to provide acceptable intravenous dosage forms for clinical use. Additionally, these three crystalline salts (1) have excellent stability both in solid form and upon reconstitution with water and (2) can be reconstituted with water to form dilute solutions (e.g. 3–5 mg/ml) of m-AMSA for intravenous administration which remain clear (no precipitation of salt) for at least several hours.

Preparation of the crystalline lactate salts of the present invention is accomplished by reacting m-AMSA base with L(+)-lactic acid, D(−)-lactic acid or DL-lactic acid in an acetone solvent. Upon stirring, preferably at room temperature, the desired salt crystallizes from solution and may be recovered as by filtration.

It is preferred in carrying out the above process to first obtain the m-AMSA base and lactic acid in acetone solution and then filter them before mixing to form the crystalline product. The lactic acid and m-AMSA base may be reacted in proportions of about one to four molar equivalents of lactic acid per mole of m-AMSA. For best results, however, an excess of lactic acid (preferably at least two and most preferably about 2.5 molar equivalents) is employed. The reaction may be carried out over a wide temperature range, e.g. from about 0° C. to 40° C., but is most advantageously conducted at room temperature. If desired seed crystals of the desired crystalline lactate salt may be added to the reaction mixture to induce and/or enhance crystallization. After recovery the crystalline salt is washed with acetone and dried by conventional procedures, e.g. vacuum-drying at 50° C. for 16–24 hours.

We have found that it is important in preparing the monolactate salts to avoid contaminating ions of chloride, sulfate, phosphate and carbonate in the starting materials and solvent. The presence of such ions can possibly result in (1) a reduction over time in the apparent initial solubility of the salt, (2) an increase in reconstitution time and (3) precipitation of the salt from aqueous solution upon standing.

According to another aspect of the present invention, there is provided a stable, solid, water-soluble pharmaceutical dosage form for reconstitution with water or aqueous vehicle as a stable solution of m-AMSA, said dosage form being produced by the steps of (1) forming an aqueous solution of crystalline L(+)-monolactate hemiacetonate of m-AMSA containing about 0.5 moles of acetone per mole of lactate salt, crystalline m-AMSA DL-monolactate acetone solvate containing from about 0.6 to 0.7 moles of acetone per mole of lactate salt or crystalline m-AMSA D(−)-monolactate hemiacetonate containing about 0.5 moles of acetone per mole of lactate salt; and (2) lyophilizing the so-produced aqueous solution.

Preparation of the lyophilized lactate acetonates is accomplished by simply dissolving the crystalline L(+)-monolactate hemiacetonate, D(−)-monolactate hemiacetonate or DL-monolactate acetone solvate in a suitable volume of water to form a complete solution and then subjecting the aqueous solution (after an optional filtration step) to a conventional lyophilization procedure. The lyophilized solids are found to contain about one mole of lactic acid per mole of m-AMSA and to be free of acetone. They can be easily reconstituted with water or aqueous vehicle to give at least 3–5 mg/ml true solutions of m-AMSA having excellent stability characteristics.

The crystalline monolactate acetonate salts and lyophilized products provided by the present invention exhibit substantially the same antitumor properties as the prior art m-AMSA forms. Because of their high water-solubility, however, they may be used to prepare single vial dry-fill and lyophilized clinical dosage forms for intravenous administration which do not contain an undesirable pharmaceutical vehicle such as dimethylacetamide. The new dosage forms are all suitable for rapid and convenient reconstitution with sterile water or a sterile aqueous vehicle. We have found that a 3–5 mg/ml m-AMSA activity aqueous solution of the lactate acetonate salts or lyophilized products provides a particularly preferred dosage form for intravenous administration.

The m-AMSA salts and lyophilized products of the present invention may be used to prepare oral or non-intravenous parenteral dosage forms as well as the preferred intravenous injectable product.

In the treatment of mammalian tumors, the dosage forms of the present invention may be administered either orally or parenterally but preferably parenterally, in dosages and according to regimens previously disclosed in the literature.

The following examples are given in illustration of, but not in limitation of, the present invention.

EXAMPLE 1

Preparation of L(+)-Monolactate Hemiacetonate of m-AMSA m-AMSA (400 mg) was dissolved in 35 ml of acetone after 10 minutes of stirring. To this solution there was added with stirring a solution of 450 mg (4 equivalents) of L(+) lactic acid in 10 ml of acetone. An aliquot of the resulting mixture was glass rod-scratched in a small glass test tube to form crystals. The crystals were added to the reaction mixture and the mixture was stirred for 2 hours at room temperature. The orange crystals which formed were removed by filtration, washed with 10 ml of acetone and vacuum-dried at 50° C. for 18 hours. Yield of crystalline monolactate: 0.53 grams.

Properties of mono L(+) lactate hemiacetonate (a) Melting point: 135°–143° C. (decomposition)
(b) Spectral analysis: IR, NMR and UV spectra were consistent for a solvated monolactate salt containing 0.5 mole acetone per mole of m-AMSA
(c) % $H_2O$, KF=0.64
(d) Elemental Analysis: C, 58.44; H, 5.58; N, 7.70; S, 5.95.
(e) Solubility in water: 5 mg/ml.
(f) Stability: 15 mg salt was reconstituted with 10 ml sterile water. The solution was stable for at least 24 hours and showed less than a 6% activity loss after 2 weeks' storage at 45° C.

EXAMPLE 2

Preparation of Lyophilized L(+)-Monolactate Hemiacetonate of m-AMSA

The crystalline m-AMSA monolactate hemiacetonate (10 mg) prepared according to Example 1 was dissolved in 0.5 ml sterile water in an 8.2 ml flint vial. The vial was lyophilized on a laboratory lyophilizer for 16 hours. Sterile water (0.5 ml) was added to the vial. A solution was obtained after two minutes of shaking.

This experiment was repeated using 10 mg of the monolactate hemiacetonate salt dissolved in 15 ml of sterile water. The more dilute solution is preferred for preparing lyophilized product.

EXAMPLE 3

Sterile Crystallization of m-AMSA Mono L(+) Lactate Hemiacetonate

1. Slurry 1.0 g of m-AMSA free base in 100 ml of acetone at 22°–28° C. A solution or near solution is obtained in 10 minutes.

2. Using aseptic technique, pass the acetone solution of m-AMSA through a sterile Millipore-Fluoropore or Mitex filter. Collect the filtrate in a sterile glass or stainless steel container.

Wash the filter with 15 ml of acetone and add the filtered acetone to the above filtrate. This is Solution A. Use solution A in Step 5 within 5 hours.

3. Dissolve one gram of L(+) lactic acid; q.s. to 10 ml. in acetone (100 mg/ml of L(+) lactic acid). Stir for 5 minutes.

4. Using aseptic technique pass the acetone solution of L(+) lactic acid through a sterile Millipore-Fluoropore or Mitex filter. Collect the filtrate in a sterile glass or stainless steel container. This is Solution B. Do not wash the filter.

5. With moderate stirring add 5.8 ml of Solution B to all of Solution A over a 1–2 minute interval. This represents 2.5 equivalents (0.58 g) of L(+) lactic acid. Crystals should form in 10 minutes of stirring.

If crystals do not form, sterile m-AMSA monolactate hemiacetonate seed crystals may be added or the sides of the container may be scratched with a sterile glass rod to induce crystallization.

6. Stir an additional 1 hour after onset of crystallization.

7. Remove the crystals by lint-free sterile filtration technique. Wash the crystals with 25 ml of acetone previously filtered through a sterile Millipore-Fluoropore or Mitex filter.

8. Vacuum-dry the crystals at 50° C. for 16–24 hours. Yield of m-AMSA mono L(+) lactate hemiacetonate salt is 1.1 g.

EXAMPLE 4

Preparation of Crystalline m-AMSA Mono DL-Lactate Acetone Solvate m-AMSA base (150 mg) was slurried in 15 ml of acetone for 15 minutes at 45° C. A small amount of insolubles were removed by vacuum filtration through a 15 cm fine glass filter. To the filtrate there was added 0.15 ml of an 80% DL-lactic acid solution with rapid stirring. Crystals formed in about 10 minutes. The mixture was then stirred an additional 30 minutes. The crystals were removed by vacuum filtration through a 15 cm fine glass filter. The crystals were then washed with 2 ml of acetone and vacuum-dried at 50° C. for 16 hours. There was obtained 180 mg of the title salt.

Properties

Elemental analysis: C, 59.05%; H, 5.55%; H, 7.85%; S, 5.88%.

% H$_2$O(KF)=1.03.

m.p. (capillary, uncorrected)=159°–166° C. (decomposition).

NMR spectrum of the product was consistent for a monolactate salt of m-AMSA containing 0.6 mole of acetone per mole of salt. The product contained as an impurity approximately 0.1 mole % of lactyl lactate salt which is formed due to the presence of up to 20% of lactyl lactic acid in ACS purity DL-lactic acid.*

The product salt may be reconstituted with water to give a 5–7.5 mg/ml solution which remains clear at 17° C. for at least 6 hours.

Reconstituted aqueous solutions of 5, 7.5 and 10 mg/ml were readily obtained with 3 minutes shaking at 75° F. Solubility of the salt in water at room temperature is at least 15 mg/ml.

*This may be avoided by using in place of the DL-lactic acid an equimolar mixture of pure L(+)-lactic acid and pure D(−)-lactic acid.

EXAMPLE 5

Preparation of Crystalline m-AMSA Mono DL-Lactate Acetone Solvate m-AMSA base (15 g) was slurried in 1.5 liters of acetone at 22°–24° C. for 10 minutes. The mixture was vacuum-filtered and the insolubles were washed with 50 ml of acetone. The wash was added to the filtrate and the filtrate then placed in a 2 liter Erlenmeyer flask. There was added over a one minute interval 10.7 ml of an 80% DL-lactic acid solution (2.5 equivalents). The reaction mixture was seeded with crystals of m-AMSA DL-lactate acetone solvate. Crystals began to form in 5 minutes. The mixture was stirred for 1 hour at 20°–23° C. Crystals were removed by vacuum-filtration and washed with 150 ml acetone. The washed crystals were vacuum-dried at 50° C. for 18 hours to give 17.8 g of title product.

Properties

NMR and IR spectra were consistent for a monolactate salt of m-AMSA having approximately 0.7 mole of solvated acetone per mole of salt. Also present were small amounts of lactyl lactate as an impurity.

Elemental analysis: C, 59.57%; H, 5.53%; N, 7.84%; S, 5.81%.

%H$_2$O(KF)=0.81.

The salt could be readily reconstituted with sterile water to form a 7.5 mg/ml solution. Aqueous solutions having concentrations of 5 and 7.5 mg/ml remained clear for at least 16 hours at room temperature (17° C.).

EXAMPLE 6

Preparation of Crystalline m-AMSA Mono DL-Lactate Acetone Solvate m-AMSA base (20 g) was slurried in 2 liters of acetone at 25° C. for 10 minutes. The mixture was vacuum-filtered and the insolubles were washed with 100 ml acetone (the wash was then added to the filtrate). There was added to the filtrate with rapid stirring over a 1 minute interval 11.45 ml of 85% DL-lactic acid (2.5 equivalents). Crystals formed in five minutes. The mixture was stirred an additional one hour. Crystals were removed by vacuum-filtration and washed with 150 ml of acetone. Upon vacuum-drying the crystals at 50° C. for 24 hours, there was obtained 25 grams of the title product.

Properties

Elemental Analysis: C, 59.95%; H, 5.35%; N, 7.61%; S, 5.85%.

IR and NMR spectra were consistent for a monolactate salt of m-AMSA having approximately 0.67 mole of solvated acetone per mole of lactate salt. Also present were small amounts of lactyl lactate as an impurity.

Solubility testing: Reconstituted aqueous solutions of 7.5 and 10 mg of the salt per ml of water remained clear for 24 hours at room temperature. A 15 mg/ml solution remained clear for 6 hours at room temperature.

EXAMPLE 7

Lyophilization of m-AMSA Mono DL-Lactate Acetone Solvate m-AMSA DL-lactate acetone solvate (180 mg; prepared in Example 6) was dissolved in 24 ml sterile water with stirring. The resulting clear (pH 4.2) solution was passed through a 1 inch 0.45 micron Millipore filter. Two ml of the filtrate was placed in an 8.2 cc flint vial and the solution was lyophilized for 24 hours.

Addition of 2 ml of sterile water to the lyophilized vial gave a 7.5 mg/ml clear solution. The solution remained clear for at least 6 hours at 17° C. Shaking of the solution on a low speed horizontal shaker gave a clear solution for up to 5 hours.

EXAMPLE 8

Sterile Crystallization of the DL-Lactate Acetone Solvate of m-AMSA

1. Slurry 1.0 gram of m-AMSA base in 100 ml of acetone at 22°–28° C. A solution or near solution is obtained in 10 minutes.
2. Using aseptic technique, pass the acetone solution through a sterile Millipore-Fluoropore or Mitex filter. Collect the filtrate in a sterile glass or stainless steel container. Wash the filter with 10 ml of acetone and add the filtered acetone to the filtrate. This is Solution A. Use Solution A in step 5 within 5 hours.
3. Dissolve 1 gram of DL-lactic acid (1.18 ml of 85% DL-lactic acid solution); q.s. to 10 ml in acetone (100 mg/ml of DL-lactic acid). Stir for 5 minutes.
4. Using aseptic technique, pass the acetone solution of DL-lactic acid through a sterile Millipore-Fluoropore or Mitex filter. Collect the filtrate in a sterile glass or stainless steel container. This is Solution B. Do not wash the filter.
5. With moderate stirring, add 5.8 ml of Solution B to all of Solution A over a 1–2 minute interval. This represents 2.5 equivalents (0.58 g) of DL-lactic acid. Crystals should form in 10 minutes of stirring. If crystals do not form, sterile m-AMSA DL-lactate acetone solvate seed crystals may be added or the sides of the container may be scratched with a sterile glass rod to induce crystallization.
6. Stir an additional 1 hour after onset of crystallization.
7. Remove the crystals by lint-free sterile filtration technique. Wash the crystals with 10 ml of acetone previously filtered through a sterile Millipore-Fluoropore or Mitex filter.
8. Vaccum-dry the crystals at 50° C. for 16–24 hours. Expected yield of DL-lactate acetone solvate is 1.1 grams.

Properties

Figure 3:
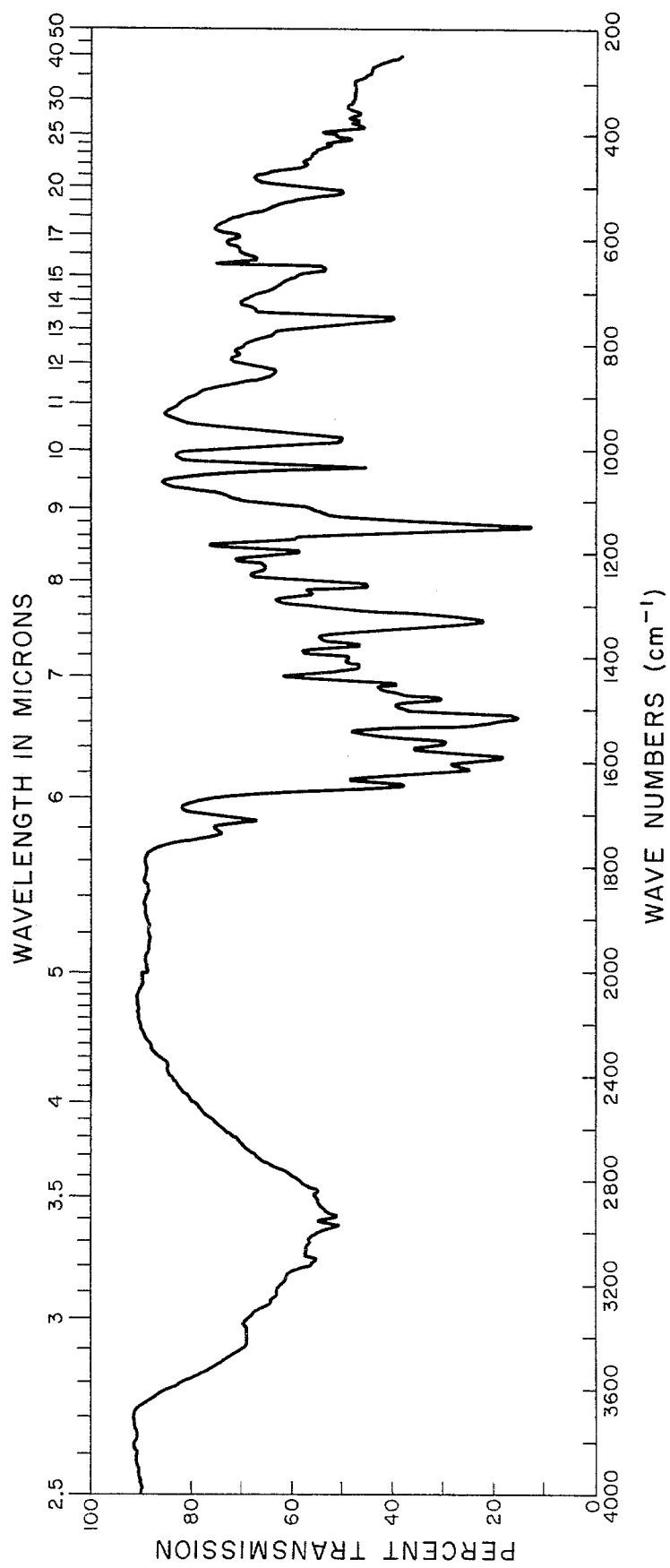
FIG. 3 shows the infrared absorption spectrum of the DL-monolactate acetone solvate of m-AMSA when pelleted in potassium bromide.
Figure 4:
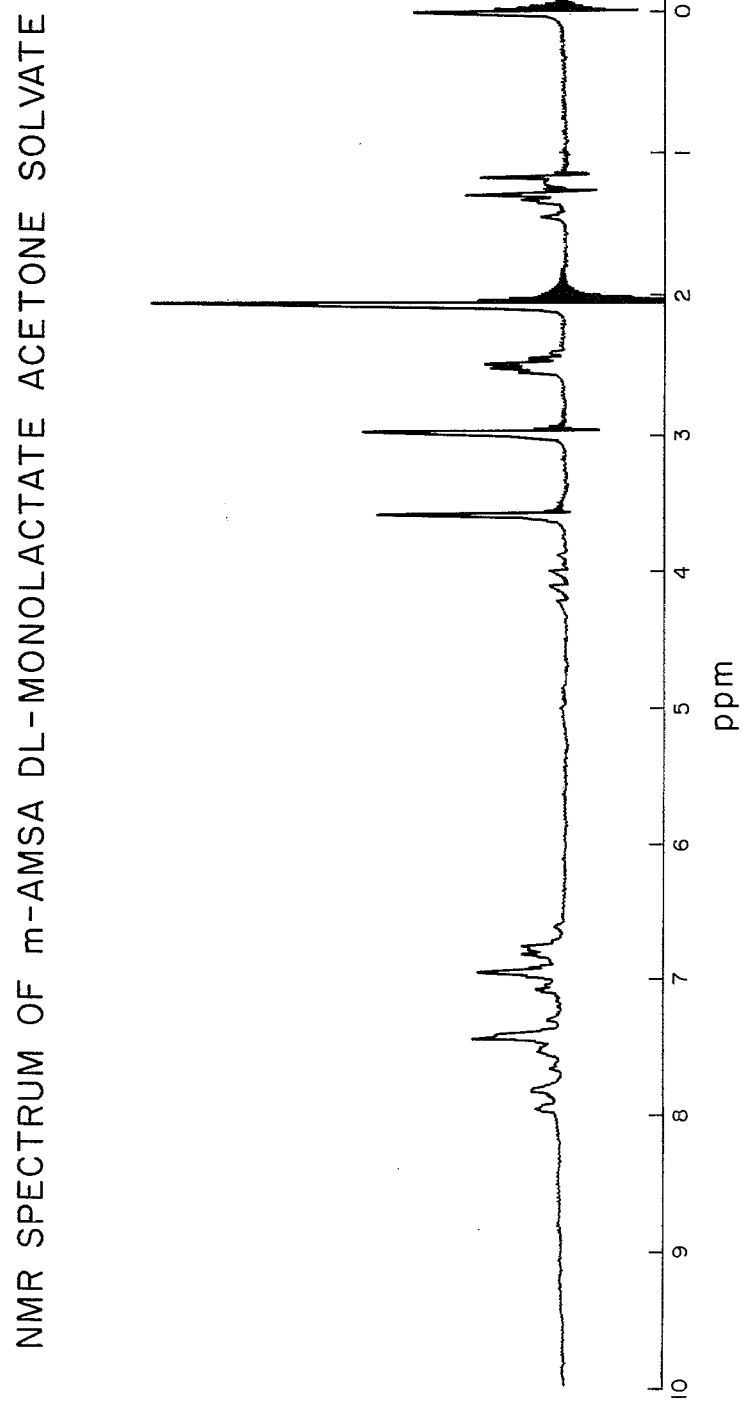
FIG. 4 shows the NMR spectrum of the DL-monolactate acetone solvate of m-AMSA in dimethylsulfoxide (100 MHz).

IR as in FIG. 3.
NMR as in FIG. 4. Shows ~0.7 mole acetone solvated to salt and approximately 0.1 mole % lactyl lactate as impurity.
m.p. = 159°–166° C. (decomp).
% m-AMSA in salt = 72% (based on HPLC assay).
Solubility in water = 25 mg/ml at room temperature.

EXAMPLE 9

Dry-fill Parenteral Formulation of m-AMSA DL-Lactate Acetone Solvate

| Ingredient | Formula* Per Vial |
|---|---|
| Sterile m-AMSA DL-lactate acetone solvate, 40–60 mesh | **0.02 gram of m-AMSA activity |

1. Using aseptic technique, place the required amount of sterile 40–60 mesh m-AMSA DL-lactate salt into sterile vials. Cap with sterile rubber enclosures. Seal with aluminum seals. Vials are stored in the dark until ready to be reconstituted.
2. For reconstitution, add a sufficient amount of sterile water for injection to give a 5 mg/ml m-AMSA activity solution. The reconstituted solutions may be stored at 20–25° C. for 16 hours. Caution: Solutions of m-AMSA are incompatible with chloride, sulfate and phosphate ions. Insoluble salts form.

*The addition of 100 mg of mannitol is found to decrease reconstitution time with water.
**The amount of m-AMSA DL-lactate acetone solvate required is a function of the potency of the salt, overfill required and needle-syringe-vial holdup. For example, assuming a product having 0.7 moles acetone per mole of salt, the m-AMSA content of such product is 74.46%. Thus to provide 0.2 grams m-AMSA activity, one would need 0.27 grams of 100% pure m-AMSA DL-lactate acetone solvate. This amount is then adjusted for the actual potency of product, overfill required, etc.

EXAMPLE 10

Preparation of Crystalline m-AMSA D(−)-Monolactate Hemiacetonate

1. Slurry 1.0 gram of m-AMSA base in 100 ml of acetone at 22°–28° C. A solution or near-solution is obtained in 10 minutes.
2. Using aseptic technique, pass the acetone solution of m-AMSA through a sterile Millipore-Fluoropore or Mitex filter. Collect the filtrate in a sterile glass or stainless steel container. Wash the filter with 10 ml of acetone and add the Millipore-filtered acetone to the filtrate. This is solution A. Use solution A in step 5 within 5 hours.
3. Dissolve 1 gram of D(−)-lactic acid in sufficient acetone to provide 10 ml of acetone solution (100 mg/ml of D(−)-lactic acid). Stir for 5 minutes.
4. Using aseptic technique, pass the acetone solution of D(−)-lactic acid through a Millipore-Fluoropore or Mitex filter. Collect the filtrate in a sterile glass or stainless steel container. This is solution B. Do not wash the filter.
5. With moderate stirring add 5.8 ml of solution B to all of solution A over a 1–2 minute interval. This represents 2.5 equivalents (0.58 g) of D(−)-lactic acid. Crystals should form in 10 minutes of stirring. If crystals do not form, sterile m-AMSA D(−)-lactate acetone solvate seed crystals may be added or the sides of the container may be scratched with a sterile glass rod to induce crystallization.
6. Stir an additional 1 hour after onset of crystallization.
7. Remove the crystals by suitable lint-free sterile filtration technique. Wash the crystals with 10 ml of acetone previously filtered through a sterile Millipore-Fluoropore or Mitex filter.
8. High-vacuum dry the crystals at 50° C. for 16–24 hours. Usual yield of m-AMSA D(−)-monolactate acetone solvate is 1.1 grams.

Properties

Figure 5:
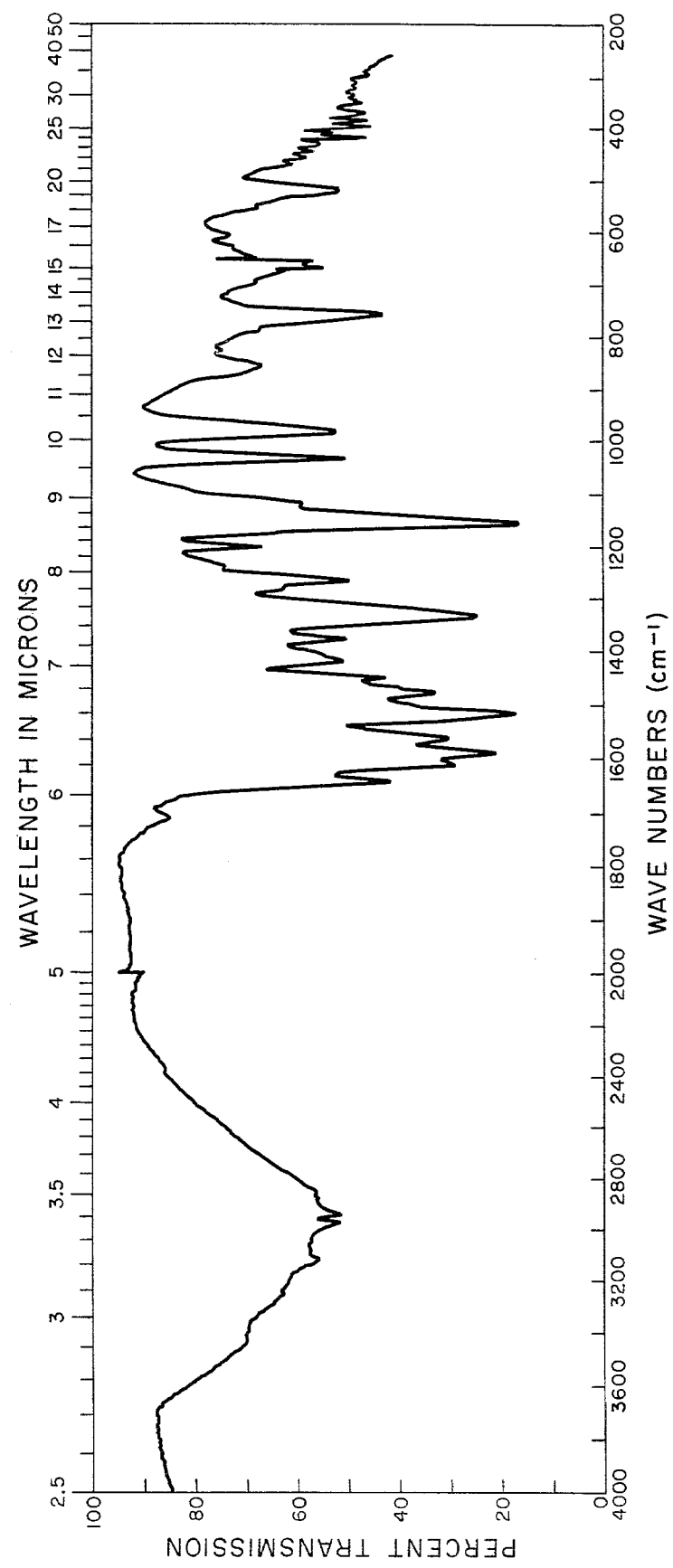
FIG. 5 shows the infrared absorption spectrum of the D(−)-monolactate hemiacetonate of m-AMSA when pelleted in potassium bromide.
Figure 6:
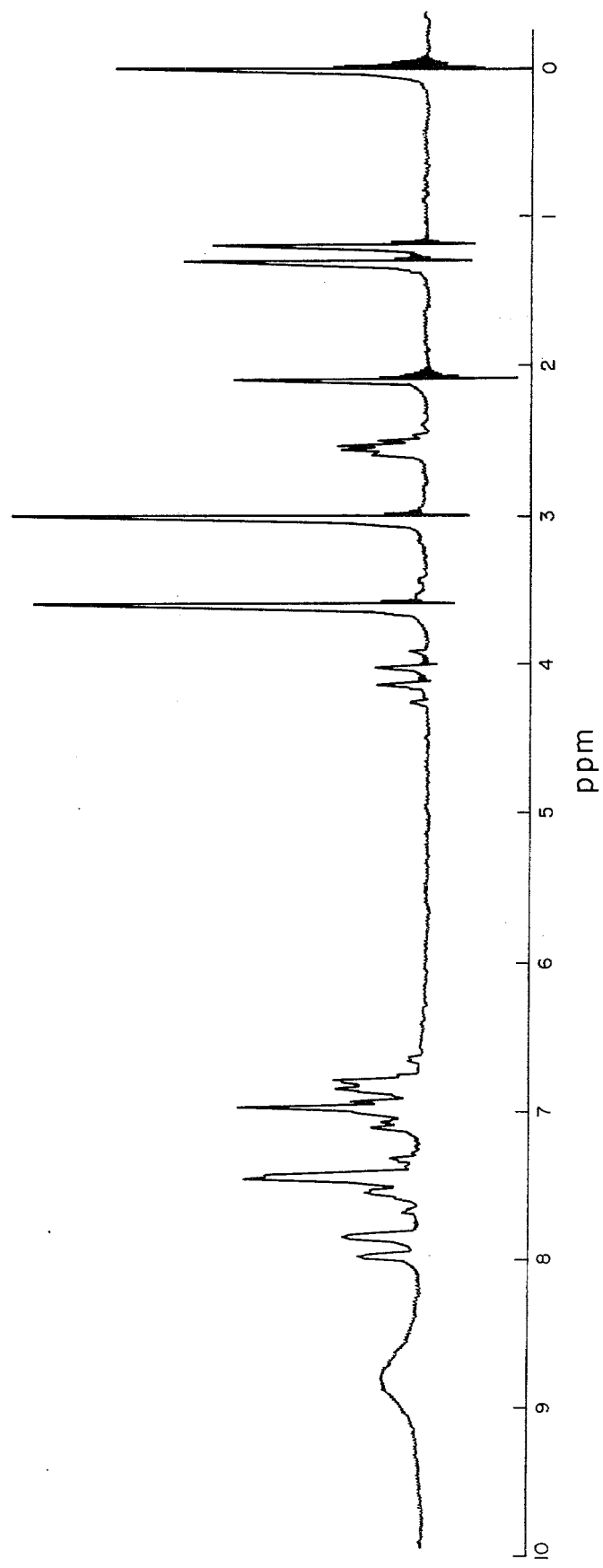
FIG. 6 shows the NMR spectrum of the D(−)-monolactate hemiacetonate of m-AMSA in dimethylsulfoxide (100 MHz).

IR as shown in FIG. 5.
NMR as shown in FIG. 6. Shows ~0.4 mole acetone solvated to salt.
m.p. (capillary, uncorrected): 180°–184° C. (decomposition).

% m-AMSA in salt: 78.4% (based on HPLC assay).
Elemental Analysis: C, 59.47; H, 5.20; N, 8.41; S, 6.46.
%H$_2$O (KF)=0.39.

EXAMPLE 11

Lyophilization of D(−)-Monolactate Acetonate of m-AMSA

If the procedure of Example 7 is repeated with the m-AMSA DL-lactate acetone solvate replaced by an equimolar amount of the m-AMSA D(−)-monolactate acetone solvate prepared in Example 10, there is produced a lyophilized solid which can be reconstituted with water to form at least a 3–5 mg/ml m-AMSA activity solution. The solid analyzes for 1 mole of m-AMSA per mole of D(−)-lactic acid and contains no acetone.

We claim:

1. The crystalline mono L(+)-lactate hemiacetonate of m-AMSA.

2. The crystalline mono DL-lactate acetone solvate of m-AMSA containing from about 0.6 to 0.7 moles of acetone per mole of lactate salt.

3. The crystalline mono D(−)-lactate hemiacetonate of m-AMSA.

4. A stable, solid, water-soluble pharmaceutical dosage form for reconstitution with water or aqueous vehicle as a stable solution of m-AMSA, said dosage form being prepared by the steps of
    (1) forming an aqueous solution of crystalline L(+)-monolactate hemiacetonate of m-AMSA, crystalline m-AMSA DL-monolactate acetone solvate containing from about 0.6 to 0.7 moles of acetone per mole of lactate salt or crystalline m-AMSA D(−)-monolactate hemiacetonate; and
    (2) lyophilizing the so-produced aqueous solution.

5. The dosage form of claim 4 prepared from crystalline L(+)-monolactate hemiacetonate of m-AMSA.

6. The dosage form of claim 4 prepared from crystalline m-AMSA DL-monolactate acetone solvate containing from about 0.6 to 0.7 moles of acetone per mole of lactate salt.

7. The dosage form of claim 4 prepared from crystalline m-AMSA D(−)-monolactate hemiacetonate.

* * * * *